United States Patent
Falotico et al.

(10) Patent No.: US 8,887,477 B2
(45) Date of Patent: Nov. 18, 2014

(54) E BEAM STERILIZATION OF MEDICAL DEVICES COMPRISING BIOACTIVE COATING

(75) Inventors: Robert Falotico, Belle Mead, NJ (US); Chengxue Li, Fremont, CA (US); Thai M. Nguyen, Santa Clara, CA (US); Theodore L. Parker, Danville, CA (US); Jonathon Z. Zhao, Belle Mead, NJ (US)

(73) Assignee: Cordis Corporation

( * ) Notice: Subject to any disclaimer, the term of this patent is extended or adjusted under 35 U.S.C. 154(b) by 865 days.

(21) Appl. No.: 12/619,118

(22) Filed: Nov. 16, 2009

(65) Prior Publication Data

US 2011/0113728 A1    May 19, 2011

(51) Int. Cl.
| | |
|---|---|
| B65B 31/00 | (2006.01) |
| B65B 55/00 | (2006.01) |
| B65B 55/16 | (2006.01) |
| A61L 2/08 | (2006.01) |
| B65D 81/26 | (2006.01) |

(52) U.S. Cl.
CPC ............... B65B 31/00 (2013.01); B65B 55/00 (2013.01); B65B 55/16 (2013.01); A61L 2/087 (2013.01); A61L 2202/21 (2013.01); B65D 81/266 (2013.01)
USPC .............. 53/400; 53/425; 53/432; 250/492.3; 422/22

(58) Field of Classification Search
CPC ......... A61L 2/087; A61L 31/10; A61L 31/16; A61L 2202/181; A61L 2202/21; A61L 2202/24; B65B 31/00; B65B 55/02; B65B 55/16; B65B 55/18
USPC .......... 53/400, 425, 432, 434; 422/22, 28, 33, 422/40; 250/455.11, 492.3
See application file for complete search history.

(56) References Cited

U.S. PATENT DOCUMENTS

| | | | |
|---|---|---|---|
| 4,656,083 | A | 4/1987 | Hoffman et al. |
| 5,034,265 | A | 7/1991 | Hoffman et al. |
| 5,132,108 | A | 7/1992 | Narayanan et al. |
| 5,244,654 | A | 9/1993 | Narayanan |
| 5,409,696 | A | 4/1995 | Narayanan et al. |

(Continued)

FOREIGN PATENT DOCUMENTS

| | | |
|---|---|---|
| EP | 1518563 | 3/2005 |
| WO | 2006/130826 | 12/2006 |
| WO | 2008/021481 | 2/2008 |

OTHER PUBLICATIONS

Kocsis, J., et. al. "Heparin-Coated Stents", Journal of Long-Term Effects of Medical Implants, vol. 10, pp. 19-45 (2000).

(Continued)

*Primary Examiner* — Stephen F Gerrity

(57) ABSTRACT

The invention provides a method for single-step terminal sterilization process for bio-active heparin coatings on materials and biomaterials containing heparin used in medical devices, such as catheters, tissue engineering scaffolds, or drug delivery carrier materials. This may include any medical device or implantable that could benefit from improved antithrombotic and biocompatible heparin surfaces. Other relevant device examples may include heparin or a heparin derivative coated stents to reduce clotting and restenosis, dental or ophthalmological implants. These materials may comprise additional polymeric compositions such as polyethyleneimine, dextran sulfate or their modified forms. These polymers together with heparin coatings may be applied to other substrate of medical devices such as metal, ceramics or biologically derived materials.

9 Claims, 2 Drawing Sheets

(56) References Cited

U.S. PATENT DOCUMENTS

| | | |
|---|---|---|
| 6,787,179 B2 | 9/2004 | Timm et al. |
| 7,303,758 B2 * | 12/2007 | Falotico et al. ............... 424/424 |
| 2004/0187438 A1 * | 9/2004 | Clarke et al. .................. 53/400 |
| 2006/0260967 A1 * | 11/2006 | Clarke et al. .................. 206/438 |
| 2007/0084144 A1 * | 4/2007 | Labrecque et al. ............. 53/425 |
| 2007/0280851 A1 * | 12/2007 | Freeman et al. ................. 422/1 |
| 2008/0010947 A1 * | 1/2008 | Huang et al. ................... 53/425 |
| 2008/0075628 A1 * | 3/2008 | Judd et al. ....................... 422/22 |

OTHER PUBLICATIONS

Palmaz, J., et a. "Intravascular Stents", Advances in Vascular Surgery, vol. 1, pp. 107-135 (1993).

European Search Report in corresponding patent application No. EP10187304 dated Jan. 27, 2011, 6 pages.

* cited by examiner

Effect of E beam dose on the heparin activity as measured by antithrombin III Uptake assay (AT III uptake).

Effect of E beam dose on the heparin activity as measured by anti factor Xa assay (FXa inhibition assay).

Effect of E beam dose on the heparin surface density.

E BEAM STERILIZATION OF MEDICAL DEVICES COMPRISING BIOACTIVE COATING

BACKGROUND OF THE INVENTION

1. Field of the Invention

The present invention relates to medical devices comprising bioactive coatings, and more particularly, to methods of sterilizing medical devices comprising bioactive coatings, while in their packaging, utilizing E beam sterilization techniques.

2. Description of the Related Art

Numerous metallic materials and polymeric materials have been utilized in the fabrication of implantable medical devices as well as coatings on implantable medical devices. Surface modifications and coatings of the same or different compositions are frequently used to further improve the biocompatibility and hemocompatibility of the implantable medical devices. The modification or coating of these devices typically requires several processing steps to complete. Substrates modified by each of these processes as well as the surface coatings require some manner of sterilization to ensure the sterility of the products for use in a patient. Currently utilized sterilization processes for bare metal devices may have potential drawbacks, for example, diminished coating stability, when utilized on coated devices, as the coating materials may not be compatible with these traditional sterilization methods.

Different methods of surface modification have been documented in the literature for the purpose of favorable host-material response. Several United States patents describe means and methods for coating medical devices, particularly those in contact with blood such as stents, but do not address the problem of subsequent sterilization (U.S. Pat. Nos. 4,656,083; 5,034,265; 5,132,108; 5,244,654; and 5,409,696). Palmaz et al., in a review of intravascular stents, are skeptical of the use of stent coatings (Palmaz, J., F. Rivera and C. Encamacion. Intravascular Stents, *Adv. Vasc. Surg.*, 1993, 1:107-135). However, Kocsis et al. report that the use of heparin-coated stents was effective to reduce thrombogenicity of the stent surface (Kocsis, J., G. Llanos and E. Holmer. Heparin-Coated Stents, *J. of Long-Term Effects of Medical Implants*, 2000, 10 19-45).

Typical surface modifications include hydrophilic and/or hydrogel coatings such as polyvinyl pyrrolidone (PVP), polyethylene glycol (PEG), or Hyaluronic acid (HA), on the surface of cardiovascular implants, such as stents and pacemakers, or indwelling medical devices, topical wound healing applications, contact lenses, intraocular lenses, and the like. Hydrophobic or lubricious coatings are used for medical devices such as coronary or neurovascular guidewires, sutures, needles, catheters and trocars. Bio-active coatings are used for directed cell response such as cell adhesion molecules (CAM, such as RGD (amino acid sequence Arg-Glu-Asp), laminin, collagen, and the like) in tissue engineering applications or adhesion prevention coatings to be used on medical devices such as vena cava filters or small diameter vascular grafts. Coating materials also include infection resistance agents or antimicrobial agents. Some coatings also provide for sustained drug release such as sustained release of drug from stents, or as a hydrophobic overcoat to extend the release time of a drug loaded depot. Bio-active coatings containing therapeutic agents such as heparin, phosphoryl choline (PC), urokinase, and the like, are used for antithrombogenic properties.

The coatings may be used to deliver therapeutic and pharmaceutical agents including antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); Angiogenic: vascular endothelial growth factor (VEGF), fibroblast growth factor (FGF); nitric oxide donors; anti-sense oligo nucleotides and combinations thereof.

Coatings may be formulated by mixing one or more therapeutic agents with the polymeric coating mixture. The therapeutic agent may be present as a liquid, a finely divided solid, or any other appropriate physical form. Optionally, the coating mixture may include one or more additives, for example, nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide (PO), PVP, PEG, carboxymethyl cellulose, and hydroxymethyl cellulose to a hydrophobic (co)polymer coating to modify the release profile. Appropriate relative amounts may be determined by monitoring the in vitro and/or in vivo release profiles for the therapeutic agents.

Methods for surface modification typically include a surface activation step followed by the coupling of the desired molecule. Surface activation is usually achieved by an energy assisted gas phase reaction (plasma, pulsed plasma, flow discharge reactive chemistry (FDRC), corona discharge, etc.) and/or activating the substrate with a highly reactive leaving group (N—OH succinimide, imidazole, etc.); Functionalization of the surface with self-assembly molecules (SAM, functional silanes and thiols); Controlled hydrolysis of the esters and amides at the surface (polyethylene terephthalate (PET), polylactic acid (PLA), polyglycolic acid (PGA), etc.). Coupling reactions are typically accomplished by carbodiimide chemistry, reductive amination, malemide-thiol reactions, etc.

Photochemical surface modifications are usually preferred since this method typically does not require a prior surface activation step. Arylketone based chemistry, azide chemistry, acrylate chemistry are key examples.

Regardless of the type of coating, sterilization of the final product, as stated above, may cause potential problems. Conventional sterilization methods such as hot steam, radiation (gamma and E beam), and ethylene oxide may negatively impact the activity of the coating. For example, medical devices are normally sterilized by a terminal sterilization process such as ethylene oxide (EtO) sterilization, gamma sterilization, or more recently E beam sterilization. EtO sterilization is mild toward metal and polymer based medical products such as catheters, bare metal stents and early generation drug eluting stents. It is a long and often cumbersome process that needs fine tuning of process parameters such as duration, temperature, humidity, the ratio between carrier gas and moisture, and extensive degassing processes to remove the residual EtO after the process, More importantly, the very mechanism by which EtO kills pathogens (the disruption of the nucleic acids) in the presence of moisture may also be detrimental to sensitive chemical compounds and most biological molecules. Proteins, peptides and gene products are most prone to destruction of EtO. Gamma sterilization which does not involve moisture is extremely energy intensive to be useful in sterilizing most biological containing devices and drug device combination products. E beam, sterilization, which is electrically generated gamma radiation, is also energy intensive and is also known to be potentially destructive to many biologics.

Ethylene oxide sterilization (EtO mixed with water vapor) has been known to decrease the activities of biologically active surfaces such as heparin coated surfaces. In addition, the presence of water vapor in the EtO process is also known to have a negative impact the shelf life of sterile medical devices containing heparin surfaces. Other energy intensive processes such as gamma and E beam sterilization processes have been shown to cause a decrease in the activity of bioactive coatings, see for example U.S. Pat. No. 6,787,179.

Experience with heparin coated stents and EtO sterilization has shown that in this type of sterilization process, it is difficult to control and may cause a significant decrease in heparin activity. EtO may also cause fluctuations of the heparin activities from one manufacturing site to another. Small changes of EtO sterilization conditions could lead to a wide variation of heparin activity and consequently the release specification and shelf life of heparin coated stents.

In the era of the drug eluting stents, heparin and other bioactive coatings or surfaces will be in close vicinity of a drug such as sirolimus and the drug carrier such as PLGA polymers. In addition to the sensitivity of heparin towards EtO, both sirolimus and biodegradable polymers are known to retain substantial amounts of EtO post-processing. It is therefore advantageous to use alternative methods such as E beam to terminally sterilize heparin coated drug eluting devices. In the literature, it is generally not advised to use high energy process such as E beam to sterilize a biologics containing pharmaceutical and/or drug device combination products. Instead, expensive aseptic manufacturing, filtration/lyophilization processes are commonly used to ensure sterility of the final packaged products.

Given the above limitations of conventional sterilizations including ethylene oxide, E beam and gamma radiation processes, they have not been routinely used to sterilize medical devices that contain a biologically active component such as a heparin coating. Accordingly, there exists a need for a convenient terminal sterilization process that ensures both the sterility of a medical device and the activities of its biological coating.

SUMMARY OF THE INVENTION

The present invention overcomes the limitations associated with currently utilized sterilization techniques as briefly described above.

The present invention relates to methods and processing conditions of sterilizing a medical device which includes the steps of packaging and sealing medical devices with bioactive heparin coatings under vacuum and with drying agents and sterilizing the packaged medical devices and its bioactive coatings with an E beam process of a suitable dose.

The present invention is directed to an E beam process, which is an energy intensive process normally used to sterilize medical products with a biological component, which may be employed to maintain the biological activities of a surface heparin coating. Within an optimal range, E beam energy unexpectedly retains and revives the biological functions of a heparin coating. This process may also be used as an effective means of extending the shelf life of immobilized and likely free forms of heparin. The present invention has broad applications in sterilizing heparin coated medical devices and other heparin based pharmaceutical products.

The present invention also demonstrates that E beam process when properly controlled not only maintains the biological activity of the heparin coating, it also reverses the loss of heparin activity during a drug eluting stent manufacturing process that involves solvent exposure and prolonged drying at elevated temperatures. In a controlled experiment, it was also discovered that an E beam process at a 25 KGy dose recovered the lost biological activity of heparin during storage. The present invention thus may have potential for maintaining heparin in other forms, and may become a simple method of extending product shelf life by reprocessing using an E beam process.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The present invention solves a critical long-standing concern of destroying or decreasing the activity of a biological molecule, such as heparin, associated with a medical device by an E beam sterilization process. It is also far superior to more conventional sterilization techniques, such as ethylene oxide sterilization, that is known for severely decreasing the activities of a heparin coating.

An unexpected finding of the present invention is that with the processing steps utilized, the activity of a heparin coating on the surface of a medical device or in reservoirs in a medical device did not decrease as predicted by the literature and reported by others. The heparin activity as determined by both modified FXa and antithrombin binding assays, has consistently showed unexpected increases after E beam processing, proportional to the E beam dose utilized as is explained in detail subsequently.

In general, the process of the present invention comprises packaging a medical device containing a bioactive heparin surface with nitrogen and drying agents, and sterilizing the medical device by an E beam process with a suitable dose of radiation. Although the process may be utilized on any number of substrates, for ease of explanation, exemplary embodiments of the process will be described with respect to a stent.

In one exemplary embodiment of the invention the substrate material may include a metal, a non-metal, a polymer or a combination of both metals and polymers. In a preferred exemplary embodiment, the substrate material is selected from the group including stainless steel, aluminum, nitinol, cobalt chrome, and titanium and similar metal alloys. In an alternate embodiment, the material is selected from the group including glass, silica, and ceramic. A preferred embodiment includes a CoCr alloy (L605) coronary stent that also has reservoirs in the struts.

Figure 1:
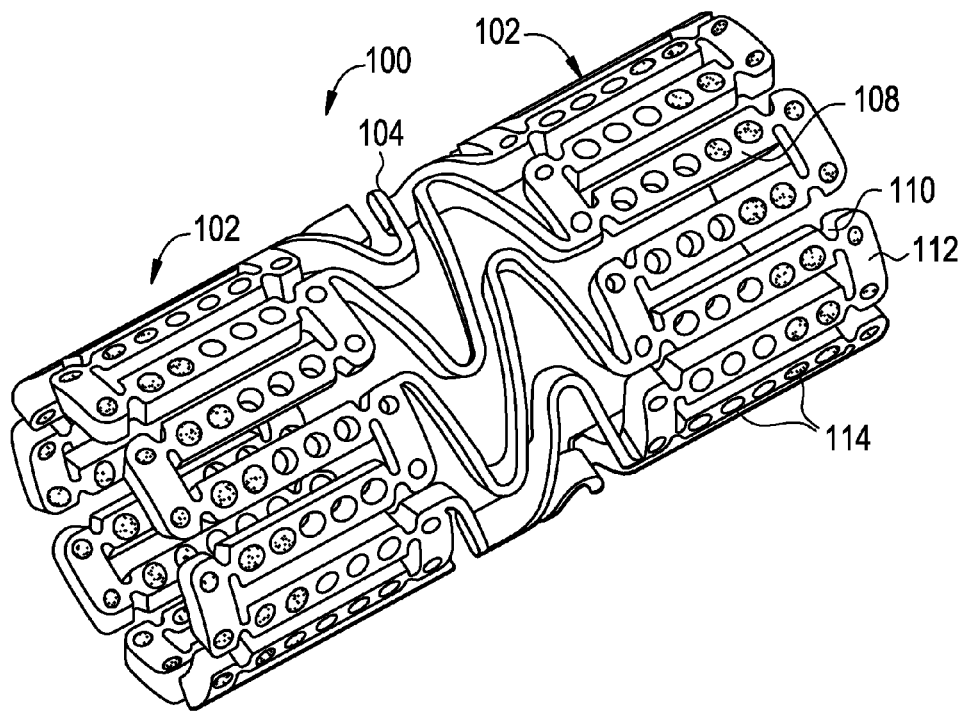
FIG. 1 is an isometric view of an expandable medical device in accordance with the present invention.

FIG. 1 illustrates an exemplary expandable medical device or stent having a plurality of holes containing a beneficial agent for delivery to tissue by the expandable medical device. The expandable medical device 100 illustrated in FIG. 1 is cut from a tube of material to form a cylindrical expandable device. The expandable medical device 100 includes a plurality of cylindrical sections 102 interconnected by a plurality of bridging elements 104. The bridging elements 104 allow the tissue supporting device to bend axially when passing through the torturous path of vasculature to a deployment site and allow the device to bend axially when necessary to match the curvature of a lumen to be supported. Each of the cylindrical sections 102 is formed by a network of elongated struts 108 which are interconnected by ductile hinges 110 and circumferential struts 112. During expansion of the medical device 100 the ductile hinges 110 deform while the struts 108 are not deformed.

As illustrated in FIG. 1, the elongated struts 108 and circumferential struts 112 include openings 114, some of which contain a beneficial agent for delivery to the lumen in which the expandable medical device is implanted. In addition, other portions of the device 100, such as the bridging elements 104, may also include openings. Preferably, the openings 114 are provided in non-deforming portions of the device 100, such as the struts 108, so that the openings are non-deforming and the beneficial agent is delivered without risk of being fractured, expelled, or otherwise damaged during expansion of the device The exemplary embodiments of the invention illustrated may be further refined by using Finite Element Analysis and other techniques to optimize the deployment of the beneficial agents within the openings 114. Basically, the shape and location of the openings 114, may be modified to maximize the volume of the voids while preserving the relatively high strength and rigidity of the struts with respect to the ductile hinges 110. According to one preferred exemplary embodiment of the present invention, the openings have an area of at least $5\times10^{-6}$ square inches, and preferably at least $7\times10^{-6}$ square inches. Typically, the openings are filled about fifty percent to about ninety-five percent full of beneficial agent.

The various exemplary embodiments of the invention described herein may provide different beneficial agents in different openings in the expandable device or beneficial agents in some openings and not in others. In other embodiments, combinations of beneficial agents or therapeutic agents may be utilized in single openings. The particular structure of the expandable medical device may be varied without departing from the spirit of the invention. Since each opening is filled independently, individual chemical compositions and pharmacokinetic properties may be imparted to the beneficial agent in each opening.

In another exemplary embodiment of the invention the substrate material may also contain additional polymeric material that serves as a matrix for controlling the release of a pharmaceutically agent in or on the medical device. The polymer may be biostable such as the group including polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, and copolymers and combinations thereof. In another exemplary embodiment of the invention the material is selected from the group including polysiloxane, fluorinated polysiloxane, ethylene-propylene rubber, fluoroelastomer and combinations thereof. The polymeric material may be biodegradable or bioresorbable such as from the group including polylactic acid, polyglycolic acid, polycaprolactone, polyparadioxanone, polytrimethylene carbonate and their copolymers, collagen, elastin, chitin, coral, hyaluronic acid, bone and combinations thereof.

In another exemplary embodiment of the invention the medical device may also contain additional bioactive materials for anti-infection resistance, antimicrobial, and enhancement of lubricity of the device.

In a preferred exemplary embodiment of the invention the medical device comprises a heparin coating and which may have additional pharmaceutically active agents embedded in the device, or on its surface, or in the reservoirs and or blind holes in the structure of the device, alone with in admix with a matrix excipient such as a polymer. The pharmaceutically active agents may be selected from the groups of anti-inflammatory drugs such as a rapamycin, for example, sirolimus, and their various derivatives and analogs. Anti-proliferative drugs such a paclitaxel and its derivatives and analogs.

In a preferred exemplary embodiment, the biologically active coating agent is an unmodified heparin, a partially degraded heparin, low molecular weight heparin (LMWH), or the various modified forms of heparin. The heparin may be permanently attached to the surface of a medical device by means of conjugation, end-point attachment, ionic complexation, salt complex with positively charges salt, and other methods known to those skilled in the field.

Coatings applied to materials may be polymerized and covalently bound to the material surface in manufacturing. The coating may be hydrophilic or hydrophobic in nature. This polymerized and grafted coating is resistant to aqueous removal (soaking and rinsing and/or implantation in aqueous environment) and may be sterilized prior to use. However, many applied coatings that are not covalently bound (van der Waals, electrostatic, surface tension) to material surfaces in processing/manufacture are not resistant to aqueous removal.

A polymerizable coating may be covalently bound to the substrate surface by further processing, while a non-polymerizable coating will not be polymerized or grafted to the surface. A further processing step, found to induce polymerization/grafting of a coating to a material surface and sterilize in one step, is sterilization processing with low temperature hydrogen peroxide gas plasma. Materials already polymerized and grafted with a coating should also be a good candidate for a further sterilizing process with a hydrogen peroxide gas plasma sterilization system.

The materials may also be metal or non-metal or elastomer. The metal material may be comprised of a variety of metals, including but not limited to, stainless steel, aluminum, nitinol, cobalt chrome, or titanium. The materials may also be elastomeric, including but not limited to polysiloxanes, fluorinated polysiloxane, ethylene-propylene rubber or fluoroelastomers. The substrates can also be inorganics, including but not limited to glass, silica, and ceramics. The material could also be biologically derived, including but not limited to, collagen, elastin, hyaluronic acid, bone, coral or chitin.

The utility and efficacy of the present invention may be illustrated through a number of examples.

Example 1

Electropolished Cobalt Chromium stents of the design illustrated in FIG. 1 were coated with surface-bound heparin. The heparin coating is covalently bound to the stent surface through a series of intermediate layers. The final heparin coating was washed with water repeatedly and has a constant final heparin surface density of about 13 ug/cm$^2$. The activity of the heparin surface was determined at about 65 pmol/cm$^2$ by a competitive antithrombin III binding assay and 0.9 Heparin Unity/stent by a modified USP FXa inhibition assay.

The reservoirs in the struts of these heparin coated stents were filled with a matrix of poly(lactide-co-glycolide) (PLGA) and sirolimus by an ink-jetting process. After drying at elevated temperatures to remove excess solvent from the PLGA/sirolimus matrices in the reservoirs, the stents were crimped onto matching catheter balloons with a pneumatic crimper and placed in plastic trays. The plastic stent trays were then placed into aluminum pouches equipped with drying agent bags. The plastic trays were then flushed with nitrogen and vacuumed to remove any remaining air and moisture. The process is repeated three times and the pouch was sealed by a hot press sealer.

The vacuum-sealed pouches were then sterilized by an E Beam sterilizer at various doses: 10 KGy, 25 KGy, and 40 KGy. Three stents were utilized in the process for heparin density and activity determinations at each processing point and E beam dose. The stents with heparin surface in the vacuum packaged plastic pouches were returned for heparin, density and activity assays. The results are illustrated in FIG. 2 (AT uptake) and FIG. 3 (FXa inhibition assay).

Figure 2:
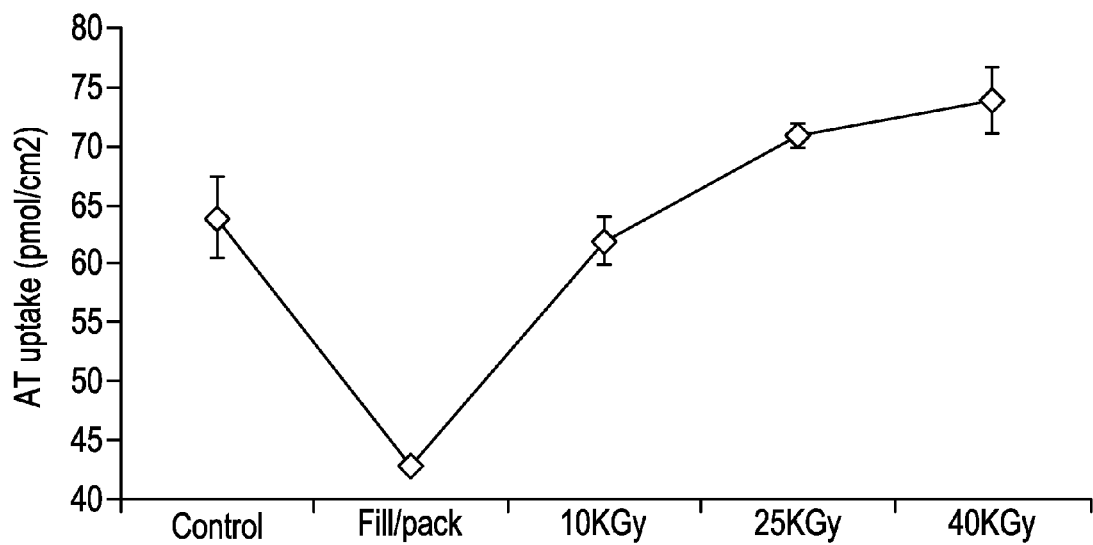
FIG. 2 is a graphical representation of the effect of E beam radiation on heparin activity as measured by the antithrombin III uptake assay in accordance with the present invention.

The data in FIG. 2 clearly demonstrates that there is a temporary decrease of heparin activity from about 65 to about 43 pmol/cm$^2$. The decrease is likely caused by the exposure to processing solvent such as DMSO and elevated temperature used to drive off excess solvent. However once the stents were vacuum packed with additional drying agent and sterilized by E beam radiation, the heparin surface regained its original activity. In addition, there also seemed to exist a positive correlation with the E beam dose used in the sterilization process, with a higher E beam dose leading to a higher specific heparin activity. These findings are quite surprising and unexpected given all the literature reports of destroyed or decreased activity of a bioactive coating after an energy intensive sterilization process such as gamma and E beam sterilization. The E beam sterilization under carefully controlled conditions even achieved a higher AT uptake value compared to the control sample that is stored at room temperature, as illustrated in FIG. 2. The findings seemed to suggest that there exists a combination of processing conditions wherein careful control of packaging parameters such as vacuum drying and additional drying agents inserted into the pouches would prevent the heparin surface and similar bioactive surfaces from losing their activity after the terminal sterilization process. The increased heparin activity with increasing E beam dose is likely caused by conformational changes of heparin during the energy intensive sterilization. This hypothesis is indirectly supported by a later experiment in which the heparin coating showed a higher AT uptake activity after E beam sterilization even though the heparin surface was not subjected to exposure to solvent (DMSO, IPA, etc.) and a high temperature (55 C). Thus there is a set of processing conditions to ensure sterility of a medical device and the activity of bioactive surface that is prone to degradation under conditions of conventional sterilization processes such as steam, ethylene oxide, or gamma methods.

Modified USP anti-factor X assay of a heparin surface directly measures the combined ability of a heparin surface and the free forms of the heparin surface released from the surface into the testing solution. The data illustrated in FIG. 3 demonstrates that the E beam process under the current carefully controlled conditions is effective in retaining and even reversing the heparin activity loss during the drug filling process. The curve differs from trend in FIG. 2 in that the control has a relatively low anti-FXa activity compared to the products at later stage of the manufacturing. This trend points to the important of using a carefully controlled packaging and E beam process to ensure good heparin activity in the final sterile product.

Figure 3:
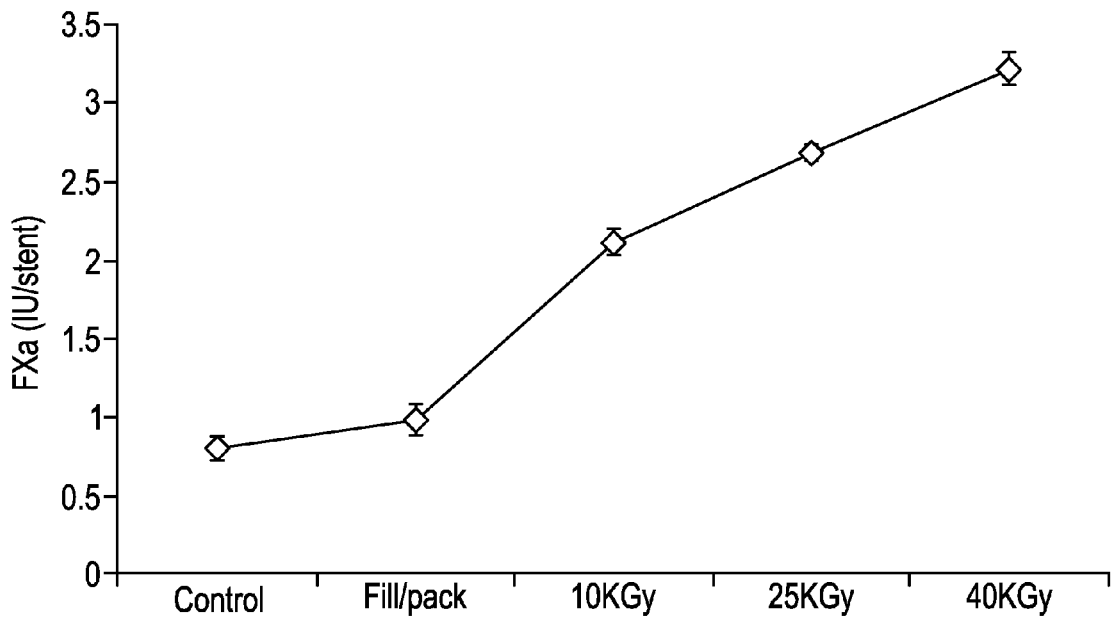
FIG. 3 is a graphical representation of the effect of E beam radiation on heparin activity as measured by the anti factor Xa assay in accordance with the present invention.

The data in FIGS. 2 and 3 point to the key aspects of the current invention in which a dose response curve of heparin activity may be maintained after optimal packaging and an E beam sterilization processes. A higher dose of E beam may be used to achieve a higher level of heparin activity in the final sterile package if needed. Since the packages are sterilized sealed, it is also feasible to use an E beam process to extend the shelf life of heparin surface after various length of storage.

Figure 4:
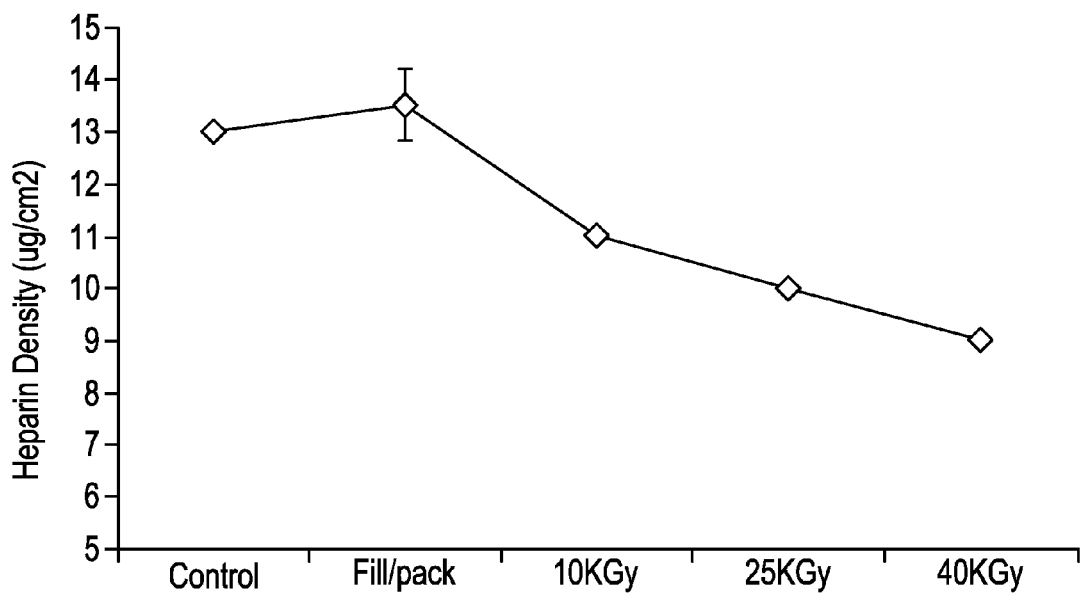
FIG. 4 is a graphical representation of the effect of E beam radiation on heparin surface density in accordance with the present invention.

The results illustrated in FIG. 4 shows that there is a gradual decrease of heparin surface density after an E beam process, with a higher E beam dose leading to a large loss of heparin density. The finding is not surprising in that the energy intensity E beam process likely caused some chain searing of heparin from the surface, with a higher dose leading to a higher extent of heparin detachment from the stent surface. The next invention thus should be tempered to an optimal range where in heparin activity is ensured while the extent of heparin content loss is minimized. In the ranges tested the loss of heparin content did not affect the heparin activity of the remaining heparin surface. The traditional E beam dose of 25 KGy seems to be in the optimal range to ensure sterility while maintaining a high level of heparin activity.

Example 2

In this study, heparin coated stents were subjected nine cycles of DMSO exposure which mimics the real processing conditions of a drug-filling process used in the manufacturing of drug eluting stent. The solvent DMSO mixed with heparin coating on the stent surface after each exposure was removed with a combination of conditions such as during for one hour at either room temperature or at 55 C followed by twenty-four hours annealing at either room temperature or at 55 C. After these lengthy solvent treatment and removal processes, the stents with heparin coatings were vacuumed packaged with drying agents and sterilized by an E beam process at 25 KGy dose. The heparin activity of stents undergoing various conditions was determined by standard AT III uptake assay.

TABLE 1

Effect of DMSO, temperature, and E beam combination on heparin activity

| | PROCESS | | | | TESTS | |
|---|---|---|---|---|---|---|
| TEST GROUP (N = 3) | Immerse in DMSO for 1 minute for each cycle. 9 cycles total | 1 hr of Drying @ | 24 hrs of Annealing @ | Sterilization | AT-Uptake | Residual Solvent |
| A | No | No | No | No | 51 | N/A |
| B | yes | Room Temp | Room Temp | No | 54 | <LOQ |
| C | yes | 55 C. | 55 C. | No | 39 | <LOQ |
| D | No | No | No | yes | 90 | N/A |
| E | yes | Room Temp | Room Temp | yes | 88 | <LOQ |
| F | yes | 55 C. | 55 C. | yes | 72 | <LOQ |

The data in Table 1 demonstrates that compared to baseline AT uptake value of 51 pmol/cm$^2$ of the control heparin surface, prolonged drying at a high temperature (55 C) decreases heparin activity to about 39 pmol/cm$^2$. The data also suggests that DMSO exposure alone does not seem to affect heparin activity if it is completely removed afterwards. The data confirmed that an E beam sterilization process is effective in maintaining heparin activity after drying at both room temperature (group B vs. group E) and at a higher temperature (group C vs. group F). The data also suggests that E beam sterilization even revives the lost heparin activity after the coating was stored at room temperature for a long time (group A (control) vs. E beamed control (group D)). Based on these findings it is reasonable to suggest that the present invention may be used to revive the heparin activity on packaged medical devices after various storage lengths.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. A method of sterilizing a medical device having a heparin coating, wherein the heparin coating is applied to the medical device with a drug filling process, the method comprising the steps of:
   placing the medical device in a package having a drying agent therein;
   flushing the package with a non-reactive gas at least one time;
   creating a vacuum within the package at least one time to remove any remaining gasses and moisture;
   sealing the package; and
   exposing the package and the medical device to one or more doses of electron beam radiation for a predetermined period of time and at a predetermined dose level and temperature, the one or more doses of electron beam radiation reversing the heparin activity loss during the drug filling process of the heparin coating.

2. The medical method of claim 1, wherein the device is selected from the group consisting of cardiovascular, endovascular, and neurovascular stents, drug-eluting cardiovascular, endovascular, and neurovascular stents, endovascular graft, vascular and vein stent graft, angioplasty balloon, AV shunt, oxygenators, artificial heart membranes and assisting devices, AAA devices.

3. The method of claim 1, wherein the medical device comprises a material selected from the group consisting of stainless steel, aluminum, nitinol, cobalt chromium, and titanium and the alloys of them.

4. The method of claim 1, wherein the medical device additionally comprises a material selected from the group consisting of polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, and copolymers and combinations thereof.

5. The method of claim 1, wherein the medical device additionally comprises a material selected from the group consisting of polylactic acid, polyglycolic acid, poly(lactide-co-glycolide), polycaprolactone, polyparadioxanone, polytrimethylene carbonate and their copolymers, collagen, elastin, chitin, coral, hyaluronic acid, bone and combinations thereof.

6. The method of claim 1, wherein the heparin is selected from the group consisting of unfractionated heparin, partially depolymerized heparin, low molecular weight heparin (LMWH), and other chemically or biologically modified heparin.

7. The method of claim 1, wherein the E beam dose is between 10 KGy to 40 KGy.

8. The method of claim 1, wherein the medical device additionally contains a pharmaceutically active component.

9. The method of claim 8 wherein the pharmaceutical agent is selected from an anti-proliferatives consisting of a rapamycin, a paclitaxel, and the derivatives and analogs.

* * * * *